United States Patent
Nelson et al.

(10) Patent No.: US 10,709,460 B2
(45) Date of Patent: Jul. 14, 2020

(54) CENTERING GUIDE SYSTEM FOR ARTHROPLASTY

(71) Applicant: Howmedica Osteonics Corp., Mahwah, NJ (US)

(72) Inventors: Andrew J. Nelson, New City, NY (US); Kaitlin Elizabeth Anne McClymont, Herndon, VA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 709 days.

(21) Appl. No.: 15/224,901

(22) Filed: Aug. 1, 2016

(65) Prior Publication Data

US 2018/0028202 A1 Feb. 1, 2018

(51) Int. Cl.
*A61B 17/17* (2006.01)
*A61F 2/46* (2006.01)
(Continued)

(52) U.S. Cl.
CPC .......... *A61B 17/17* (2013.01); *A61B 17/15* (2013.01); *A61F 2/4612* (2013.01);
(Continued)

(58) Field of Classification Search
CPC .......... A61B 17/1728; A61B 2017/568; A61B 17/8888; A61F 2/4612; A61F 2002/4624; A61F 2/4603
See application file for complete search history.

(56) References Cited

U.S. PATENT DOCUMENTS

| 5,030,219 A | 7/1991 | Matsen, III et al. |
| 5,234,294 A | 8/1993 | Hoppe et al. |

(Continued)

FOREIGN PATENT DOCUMENTS

| EP | 0874596 A1 | 11/1998 |
| EP | 1132050 A2 | 9/2001 |

(Continued)

OTHER PUBLICATIONS

BIOMET Comprehensive Total Shoulder System, Surgical Technique, Copyright 2014, 56 pages.
(Continued)

*Primary Examiner* — David W Bates
(74) *Attorney, Agent, or Firm* — Lerner, David, Littenberg, Krumholz & Mentlik, LLP

(57) ABSTRACT

Disclosed herein are systems and methods for identifying the proper implant for use in an arthroplasty procedure and preparing a bone surface for the placement of such implant. In one embodiment, a centering guide system includes a cannulated post and a translucent surface trial where the cannulated post includes a slit defining legs that flex to engage the post when inserted in a hole of the surface trial. The system is used to confirm a suitable implant size and place a pilot wire in preparation for implant placement. The cannulated post and the translucent surface trial provide comprehensive visibility of the glenoid surface. When inserted into the surface trial, an extension of the cannulated post beyond an articulating surface of the surface trial is minimal or nonexistent. In this way, the congruence of a reamed glenoid surface can be evaluated prior to implantation of the implant.

19 Claims, 12 Drawing Sheets

(51) Int. Cl.
*A61B 17/15* (2006.01)
*A61B 17/16* (2006.01)
*A61B 17/00* (2006.01)
*A61B 17/88* (2006.01)
*A61F 2/40* (2006.01)
*A61B 17/90* (2006.01)

(52) U.S. Cl.
CPC ........ *A61F 2/4684* (2013.01); *A61B 17/1684* (2013.01); *A61B 17/1778* (2016.11); *A61B 17/8897* (2013.01); *A61B 2017/0042* (2013.01); *A61B 2017/0046* (2013.01); *A61B 2017/00464* (2013.01); *A61B 2017/90* (2013.01); *A61F 2/4081* (2013.01); *A61F 2/4603* (2013.01)

(56) References Cited

U.S. PATENT DOCUMENTS

| | | | |
|---|---|---|---|
| 5,690,635 A | 11/1997 | Matsen, III et al. | |
| 5,716,361 A | 2/1998 | Masini | |
| 5,782,918 A * | 7/1998 | Klardie | A61C 8/0056 606/60 |
| 5,944,722 A | 8/1999 | Masini | |
| 5,971,985 A * | 10/1999 | Carchidi | A61B 17/0642 606/312 |
| 5,971,989 A | 10/1999 | Masini | |
| 6,187,010 B1 | 2/2001 | Masini | |
| 7,445,638 B2 | 11/2008 | Beguin et al. | |
| 7,547,327 B2 | 6/2009 | Collazo | |
| 7,909,834 B2 * | 3/2011 | Selover | A61B 17/8888 606/104 |
| 8,038,681 B2 | 10/2011 | Koenemann | |
| 8,142,510 B2 | 3/2012 | Lee et al. | |
| 8,147,557 B2 | 4/2012 | Lee et al. | |
| 8,147,558 B2 | 4/2012 | Lee et al. | |
| 8,328,874 B2 | 12/2012 | Lee | |
| 8,758,415 B2 | 6/2014 | Sonntag et al. | |
| 8,764,841 B2 | 7/2014 | Wyss et al. | |
| 8,979,847 B2 | 3/2015 | Belcher et al. | |
| 2005/0015097 A1 * | 1/2005 | Mujwid | A61B 17/8888 606/104 |
| 2005/0149042 A1 | 7/2005 | Metzger | |
| 2007/0005074 A1 | 1/2007 | Chudik | |
| 2007/0027417 A1 | 2/2007 | Chudik | |
| 2007/0270880 A1 * | 11/2007 | Lindemann | A61B 17/8888 606/104 |
| 2008/0269768 A1 * | 10/2008 | Schwager | A61B 17/8888 606/104 |
| 2010/0094312 A1 | 4/2010 | Ruiz Morales et al. | |
| 2010/0222827 A1 * | 9/2010 | Griffiths | A61B 17/8615 606/309 |
| 2011/0098715 A1 * | 4/2011 | Laubert | A61B 17/861 606/104 |
| 2011/0306984 A1 * | 12/2011 | Sasing | A61B 17/8888 606/104 |
| 2012/0123431 A1 * | 5/2012 | Robinson | A61B 17/7032 606/104 |
| 2012/0141034 A1 | 6/2012 | Iannotti et al. | |
| 2012/0143204 A1 | 6/2012 | Blaylock et al. | |
| 2013/0282019 A1 * | 10/2013 | Bouliane | A61B 17/7082 606/104 |
| 2015/0265292 A1 | 9/2015 | Olson | |
| 2016/0030196 A1 * | 2/2016 | Eraly | A61F 2/4612 606/96 |
| 2017/0042600 A1 * | 2/2017 | Ross | A61B 17/8888 |

FOREIGN PATENT DOCUMENTS

| | | |
|---|---|---|
| JP | 2013094331 A | 5/2013 |
| RU | 2041066 C1 | 8/1995 |
| RU | 2161454 C1 | 1/2001 |
| RU | 2004105013 A | 8/2005 |
| RU | 2285498 C2 | 10/2006 |
| WO | 9618351 A1 | 6/1996 |
| WO | 9716129 A1 | 5/1997 |
| WO | 2007035441 A1 | 3/2007 |
| WO | 2012138996 A1 | 10/2012 |
| WO | 2014138061 A1 | 9/2014 |

OTHER PUBLICATIONS

DePuy Global Advantage Shoulder Arthroplasty System, Surgical Technique, Copyright 2000, 32 pages.
DePuy Synthes Joint Reconstruction, "Global APG+ Instrumentation—Surgical Technique", Copyright 2014, 24 pages.
DJO, "Surgical Technique Foundation Shoulder System", Copyright 2009, 26 pages.
SIGMA High Performance Partial Knee, "Patellofemoral Joint Surgical Technique", Copyright 2009, 28 pages.
Smith&Nephew, Promos Standard Modular Shoulder System, "Surgical Technique", Copyright 2013, 48 pages.
Zimmer Bigliani/Flatow , The Complete Shoulder Solution Cannulated Instruments—Surgical Technique, Copyright 2005, 8 pages.
Zimmer Trabecular Metal Glenoid, Surgical Technique, Copyright 2008, 20 pages.
EPO Partial Search Report Appl. No. 17183731.3 dated Dec. 12, 2017, 1 page.

* cited by examiner

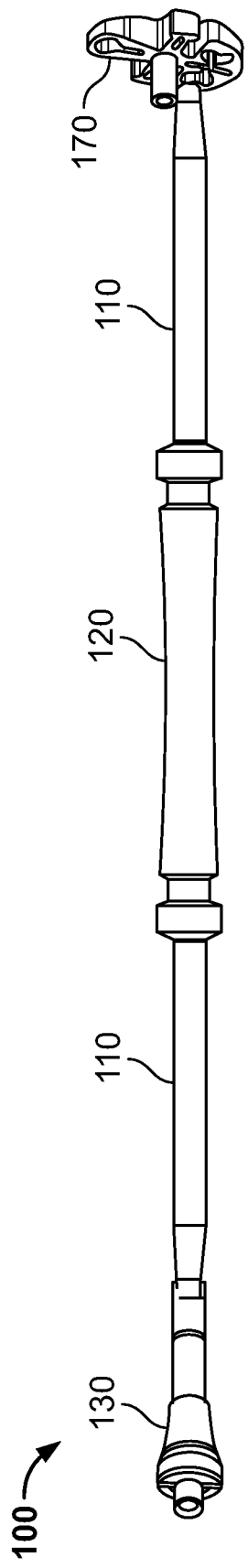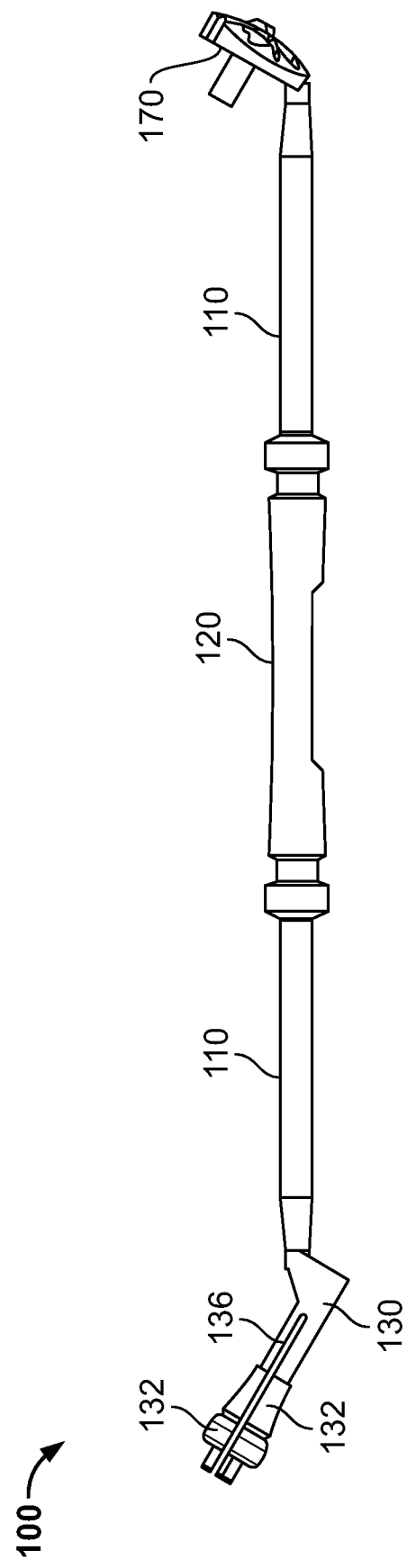
FIG. 2A
FIG. 2B

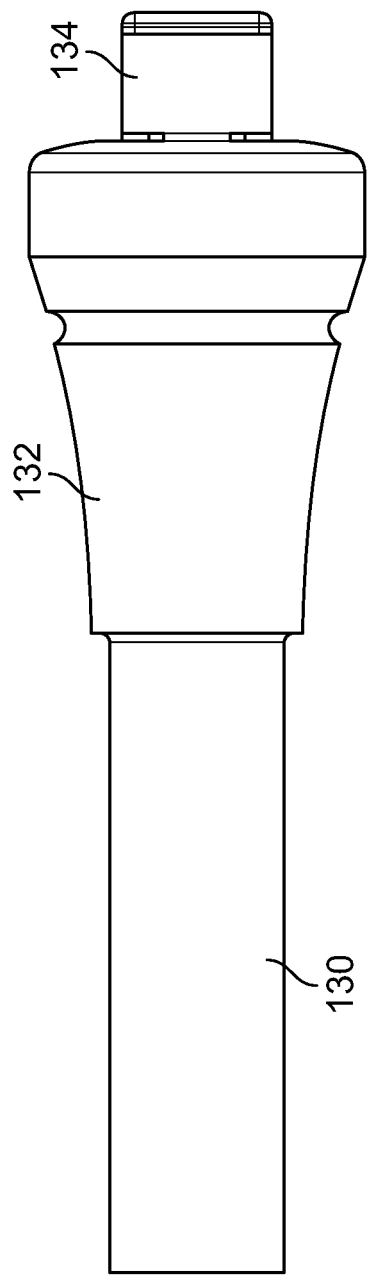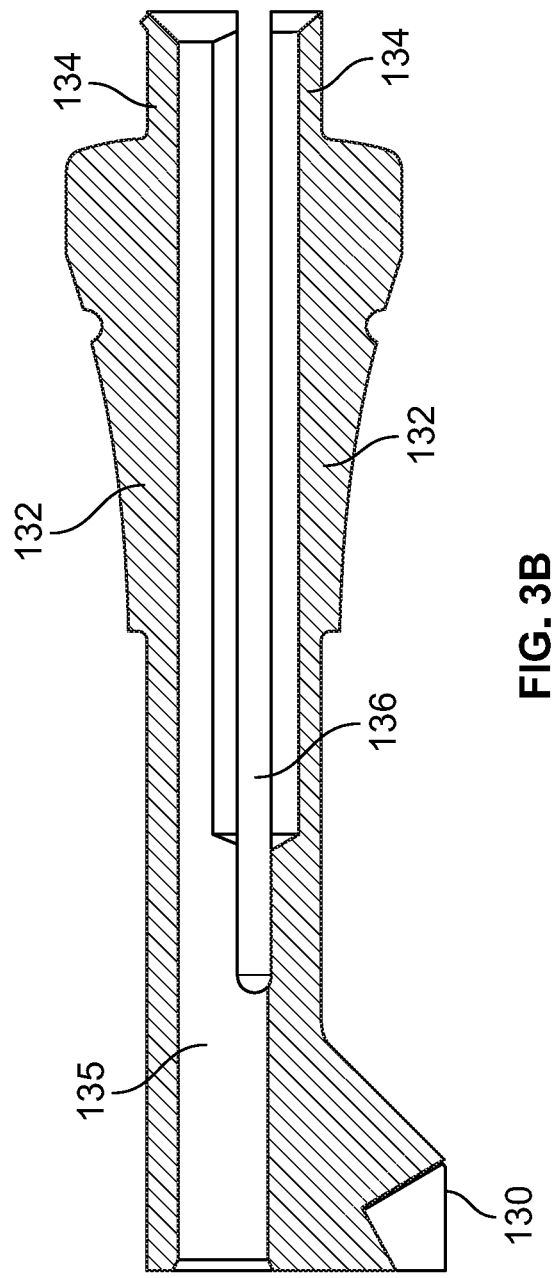
FIG. 3A
FIG. 3B

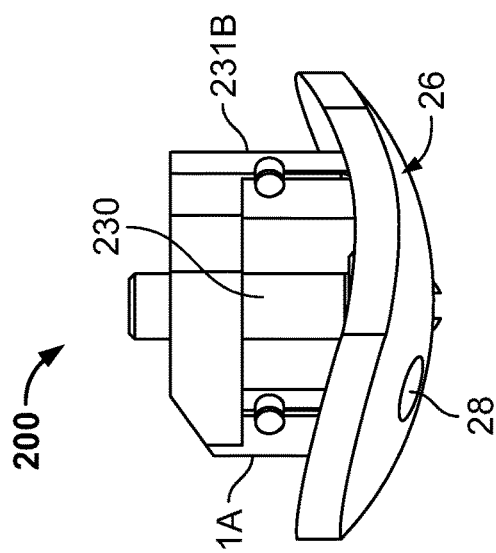
FIG. 6C
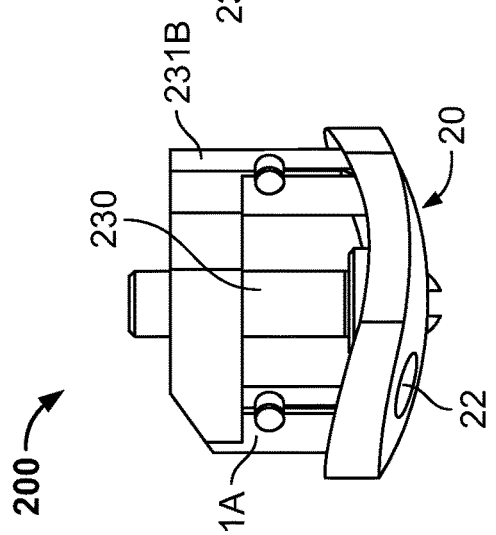
FIG. 6B
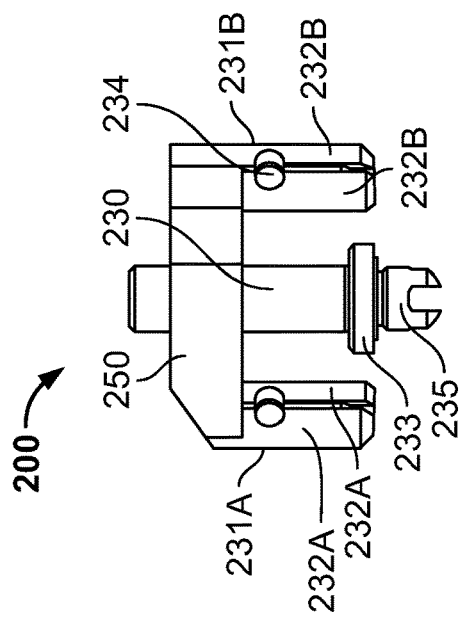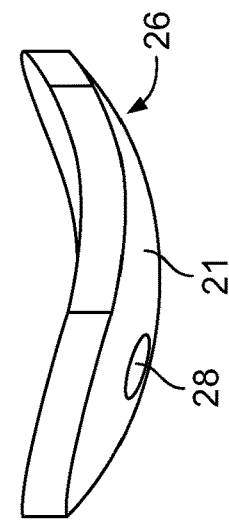
FIG. 6A

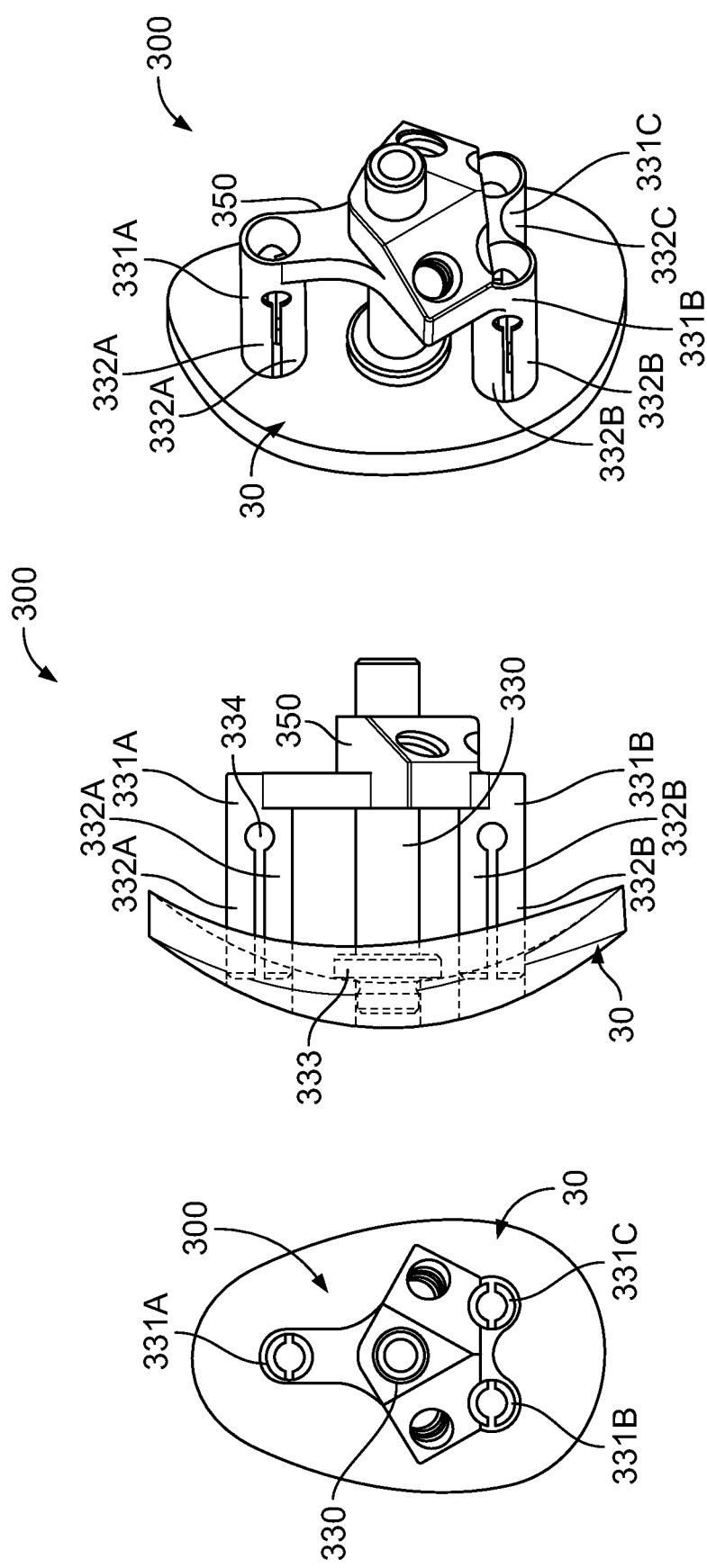

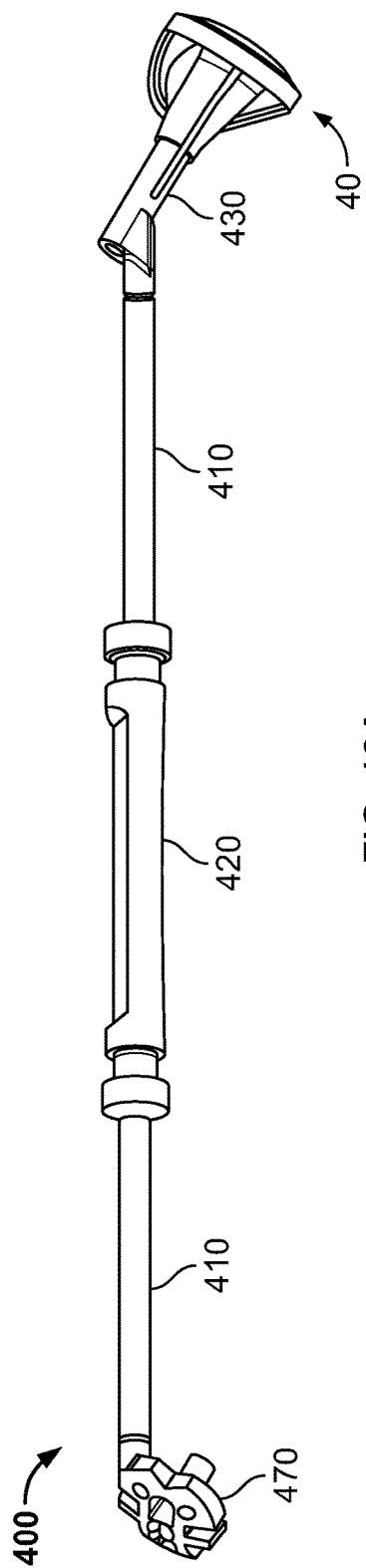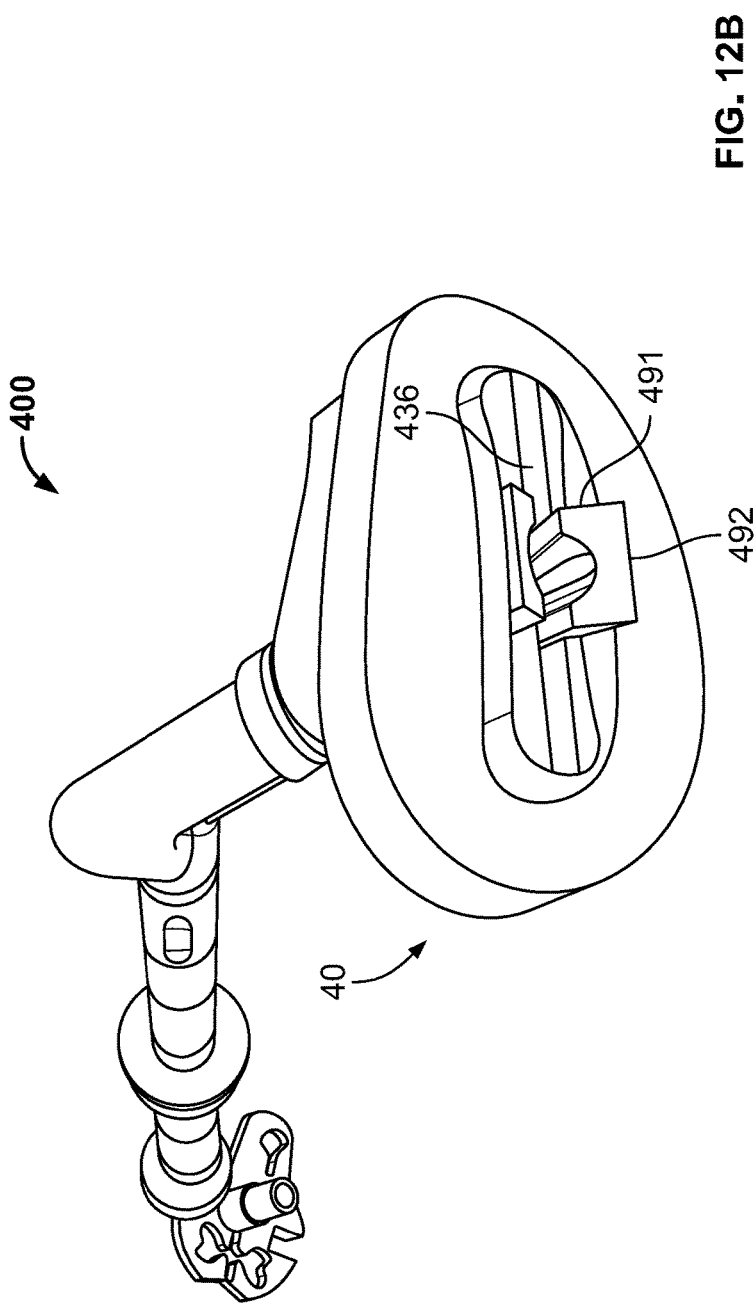

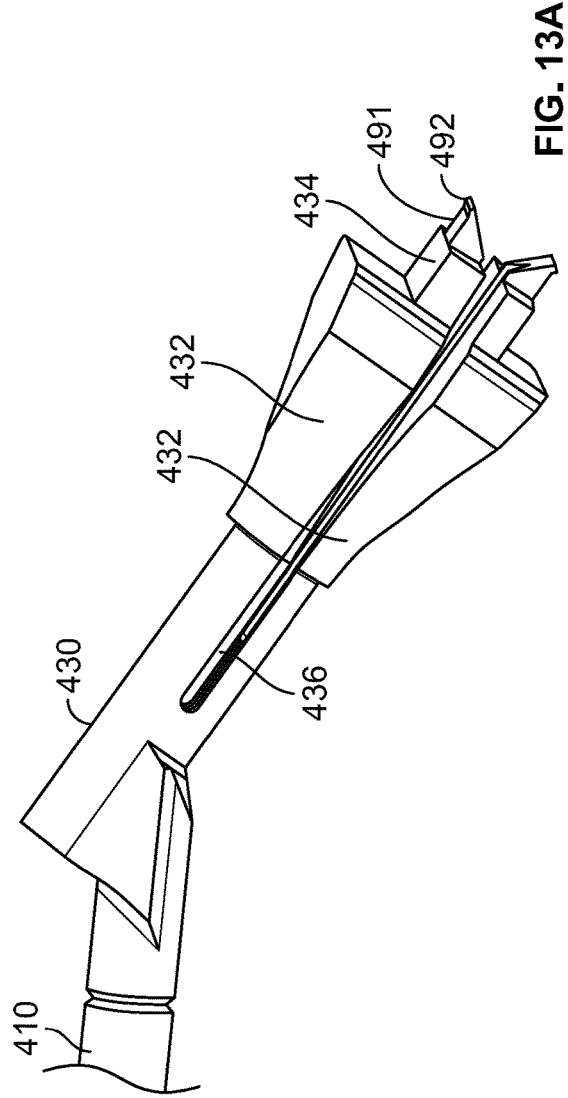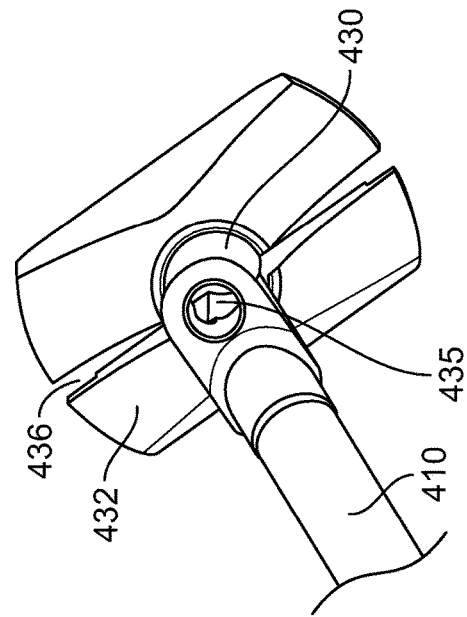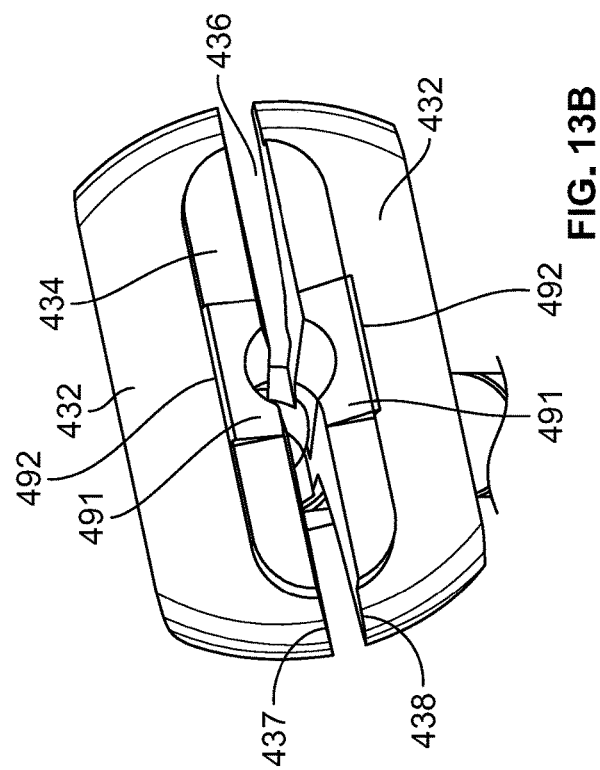

CENTERING GUIDE SYSTEM FOR ARTHROPLASTY

BACKGROUND OF THE INVENTION

During an arthroplasty procedure, corresponding bones of a joint are preferably aligned, a bone or other bones of the joint are resected as needed, and an implant is coupled to the resected bone. Before implantation of the implant into the bone, adequate preparation of a surface on the bone or bones of the joint to receive the implant is necessary. Preparation may be difficult because access to the bones can be limited by the size of the opening to the surgical site. Other reasons for difficulty include establishing alignment of the implant against a bone surface as well as the alignment of implant screw or peg locations in the resected bone. Alignment may be difficult in joints having little bone into which an implant can be placed. These challenges may be compounded by the limitations in the technique used, i.e., limited space for accessing the surgical site with a guide to resect or prepare the bone or bones of the joint.

Conventional techniques require the identification of particular tools suitable for the placement of an implant whether it be off-the-shelf or a patient-specific implant. In the context of shoulder arthroplasty procedures, centering guides may be used to drill center holes in the glenoid. Thus, such procedures are limited in that final preparation of the glenoid surface requires placement of a peg in the center of the glenoid prior to reaming. In many conventional approaches, multiple centering guides are used to complete the process of preparing the glenoid surface for implant placement. In some of those procedures and in others, the trial or implant is placed onto the glenoid surface using tongs or other instruments that grip the surface trial from its outer perimeter or from a surface facing the glenoid. In this way, when the trial or implant is placed on the glenoid surface, it is not seated flush with the bone.

Existing conventional systems and methods do not contemplate the use of a single centering guide to complete glenoid surface preparation, and many existing systems also fail to improve upon techniques to assist in the identification of center locations for the implant along with screw or peg locations. Thus, a need exists for improved glenoid centering guide systems and methods that streamline and improve the process of preparing the glenoid for the placement of an implant.

BRIEF SUMMARY OF THE INVENTION

In one aspect, the present invention relates to a guide system for resecting a bone surface in a desired location. The guide system includes a surface trial that has at least one hole. It also includes a centering guide post that is inserted into the at least one hole of the surface trial so that the centering guide post is releasably engaged to the surface trial. The centering guide post also includes a location on its length with a maximum and minimum cross sectional dimension. The cross sectional dimension at the location varies according to how far the centering guide post is positioned into the at least one hole of the surface trial. The guide system also includes a centering guide handle that is attached to the centering guide post. The centering guide handle positions the surface trial on the bone surface.

In some embodiments, the centering guide post includes a slit separating the centering guide post into first and second leg segments, the slit extending from a first end of the guide to a second location, the distance from the first end to the second location being less than a length of the centering guide post. The first and second leg segments are flexible such that a separation distance between the first and second leg segments decreases when the centering guide is placed into the at least one hole of the surface trial. In other embodiments, the surface trial is translucent. In yet another embodiment, a lip is attached to the first end of the centering guide post. The lip extends from at least a portion of an outer surface of the centering guide post. In other embodiments, the system includes a centering guide structure, the centering guide structure attached to the centering guide handle so that the centering guide handle separates the centering guide structure and the centering guide post. The centering guide structure is adapted for rigid securement with the surface trial. In other embodiments, the slit is defined by parallel interior surfaces of the first and second leg portions. The slit is located at approximately the same location on the cross section of the centering guide post at any point from the first end to the second location of the centering guide post. In yet another embodiment, the centering guide post includes at least one ball detent mechanism adapted for engagement with a surface trial.

In another aspect, the present invention relates to a guide for resecting a bone surface in a desired location. The guide includes a cannulated centering guide post. At least a portion of the centering guide post is flexible. When the centering guide post is subject to external forces applied to an outer surface on a longitudinal axis of the centering guide post, a cross sectional area of the centering guide post at one or more locations on a length of the post decreases.

In one embodiment, the centering guide post includes a slit separating the cross section into first and second leg segments. The slit extends from a first end of the guide to a second location, the distance from the first end to the second location being less than the length of the centering guide post. In another embodiment, the cannulated centering guide post includes an inner diameter defining the cannulation, the inner diameter varying along a length of the post. In yet another embodiment, the centering guide post includes a first end adapted to actively retain the surface trial when the centering guide post is inserted into the surface trial. In another embodiment, the guide includes a lip attached to the first end of the centering guide post. The lip extends outward from the outer surface of the centering guide post and is at an angle relative to the outer surface such that the lip retains the surface trial when the centering guide post is inserted through an at least one hole of the surface trial. In yet another embodiment, the guide includes a ball detent mechanism attached to the centering guide post. The ball detent mechanism is adapted to fit into a complementary shape within an at least one hole of the surface trial when the centering guide post is placed into the surface trial.

In yet another aspect, the present invention relates to a method of using a guide system for resecting a bone surface in a desired location. The method comprises steps of: using a centering guide handle to insert a first end of a centering guide post attached to the handle into a hole in a surface trial, wherein the centering guide post is adapted to engage the surface trial when inside the hole; contacting a surface of a glenoid with a contact surface of the surface trial; and placing a pilot wire through each of a cannula in the centering guide post, the surface trial and the bone.

In one embodiment, engaging the surface trial when the centering guide post is inside the hole of the surface trial further includes frictional engagement between the centering guide post and the hole of the surface trial, as the centering guide post is restrained from expanding due to an inner wall defining the hole of the surface trial. In one embodiment, engaging the surface trial when the centering guide post is inside the hole involves securement of the surface trial by a lip attached to the first end of the centering guide post, the lip extending from a body of the centering guide post in a direction distal to the centering guide post surface. In one embodiment, the method of using the guide system includes the additional steps of: removing the surface trial using the centering guide handle; inserting a reamer over the pilot wire and into the bone; removing the reamer; and replacing the system onto the bone using the centering guide handle. In yet another embodiment, inserting the first end of the centering guide post into the hole in the surface trial causes two leg segments of the centering guide post to flex so that a distance between each leg segment decreases. In another embodiment, inserting the first end of the centering guide post into the hole in the surface trial causes a boss attached to the centering guide post to become releasably engaged to an inner wall defining the hole of surface trial. In yet another embodiment, the method of using the guide system includes the additional step of viewing the surface of the bone through the surface trial after replacing the surface trial on the bone. The surface trial for this step is translucent.

BRIEF DESCRIPTION OF THE DRAWINGS

FIG. 2A shows a plan view of the guide of FIG. 1.

FIG. 2B shows an elevation view of the guide of FIG. 1.

FIG. 3A shows a top view of the centering guide shaft of the guide of FIG. 1.

FIG. 3B shows a side sectional view of the centering guide shaft of the guide of FIG. 1.

FIGS. 6A, 6B and 6C show a second embodiment of the guide at various stages of insertion into a surface trial and with a variation in surface trial sizes attached.

FIGS. 7A, 7B and 7C show a third embodiment of the guide as it appears when inserted into a surface trial from a plan, side, and perspective view, respectively.

FIG. 12A shows a plan view of another embodiment of the guide with a trial attached.

FIG. 12B shows a perspective view of the guide of FIG. 12A from an end of the guide closest to an attached trial.

FIG. 13A shows a side view of a post of the guide of FIG. 12A.

FIG. 13B shows a front perspective view of the post of the guide of FIG. 12A.

FIG. 13C shows a rear perspective view of the post of the guide of FIG. 12A.

Figure 1:
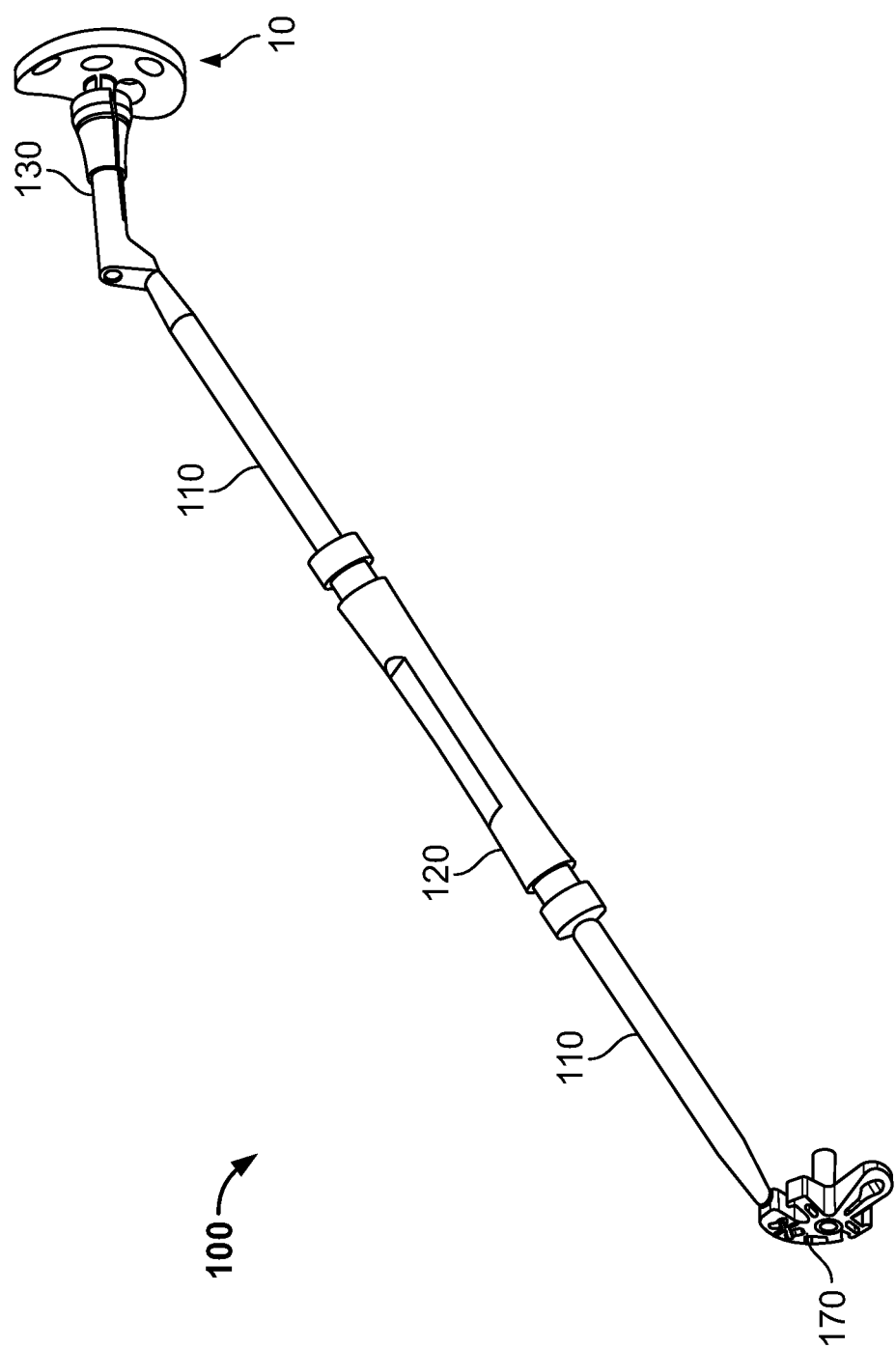
FIG. 1 shows a perspective view of one embodiment of a guide.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

This invention relates generally to a centering guide system for use in identifying a size and placement location for an implant on a bone surface. The guide is also used to prepare the bone surface for the implant. Such bones or joints that the system may be used to resect include, for example, bones of the shoulder, hip, knee, ankle and spine. The system achieves these objectives through use of a system including a guide inserted into a surface trial that is preferably translucent. Through attachment of the guide to the surface trial, the guide can be positioned in a surgical site to determine the suitability of the surface trial and to identify a location for placement of a pilot wire as well as implant fastener locations. Implant fasteners can be screws or pegs, for example. Although the embodiments described below and shown in the figures are directed to tools and surface trials for use in particular anatomical locations and for particular procedures, it is to be understood that the concepts and novelty underlying the present invention could be utilized for other types of procedures.

The term "implant" as used herein refers to a prosthetic used as part of a repair for a bone in a joint. Put another way, an artificial joint. For example, an implant on the glenoid bone of the shoulder joint is a device that is attached to the glenoid and includes an articulating surface. The term "fastener" as used herein generally refers to a device or a feature of the implant used to secure the implant to bone. For example, a fastener can be a screw or it can be a peg protruding from a surface of the implant. The term "surface trial" as used herein refers to a device having at least one articulating surface having a size and shape that emulates the implant. Particulars of the surface trial for each embodiment are as described herein or to the extent not described can be any known to those of skill in the art.

FIG. 1 illustrates one embodiment of a centering guide system of the present invention that may be used in shoulder arthroplasty. The system includes a surface trial 10 and a guide 100. The guide 100 includes a shaft 110, a centering guide handle 120 (hereinafter "handle"), a post 130 and a cross hair centering guide 170.

The surface trial 10 is translucent. In some variants, however, it can be opaque or offer other levels of visibility through its thickness. The trial is sized and contoured to fit within and match an articulating surface of a corresponding glenoid. Put another way, the translucent surface trial sits flush with a glenoid bone surface 2 when placed on it, as visible in FIG. 9, for example. In a typical procedure, many surface trial sizes are available to the user so that a size may be chosen that best reflects the needs of the patient. The surface trial 10 includes a thickness as known to those of ordinary skill in the art and also includes holes 11, 12 for visualization and for placement of the post 130 and other components of the glenoid guide 100. Each hole is defined by an inner wall forming a perimeter around the hole. In a variant, the surface trial can include only one hole. The surface trial 10 also includes a surface 13 to match the articulating surface of the glenoid.

The guide 100 as shown in FIGS. 1, 2A and 2B includes a shaft 110 with a handle 120 approaching its middle region and surrounding the shaft, with a post 130 at one end of the shaft 110 and a cross hair centering guide 170 at the other end of the shaft. These and additional details of the guide 100 are best shown in FIGS. 1-5 inclusive. The materials for each element of the guide 100 are any that are known to those of skill in the art. The geometry of the shaft 110 as shown is generally linear. The crosshair centering guide 170 is shaped and oriented to be used as a trial representing the smallest implant size. The guide can also be used as a cutting guide. The shape and orientation of the guide allows for nested placement on a target bone, such as the glenoid. In the embodiment illustrated in FIGS. 2A and 2B, the centering guide 170 includes a plurality of openings and is rigidly attached to shaft 110 at an angle of approximately 30 degrees. In some embodiments, the centering guide can have surface features and openings or other holes that vary from those shown, and the guide can be connected at an angle other than 30 degrees relative to the shaft 110 and in a manner that permits some movement relative to the shaft 110. The crosshair centering guide 170 can also be configured to provide other functions as known to those of skill in the art.

The shaft 110, as illustrated in FIGS. 1, 2A and 2B, extends linearly and includes a generally circular cross section. The handle 120 is positioned centrally within the guide so that the shaft extends linearly in both directions from the ends of the handle 120. Of course, the handle 120 can be a separate element from the shaft 110 or it can be placed circumferentially over a shaft with a length eclipsed by that of the shaft 110. At an end of the shaft 110 opposite the crosshair centering guide 170 is a singular centering guide post 130 (hereinafter "post"). The post 130 is attached to the shaft 110 in a fixed manner. Alternatively, the connection can be any type suitable to support use of the guide during surgery. The crosshair centering guide 170 and the post 130 of the guide 100 can be used in the alternative or together as part of the guide 100.

Figure 4:
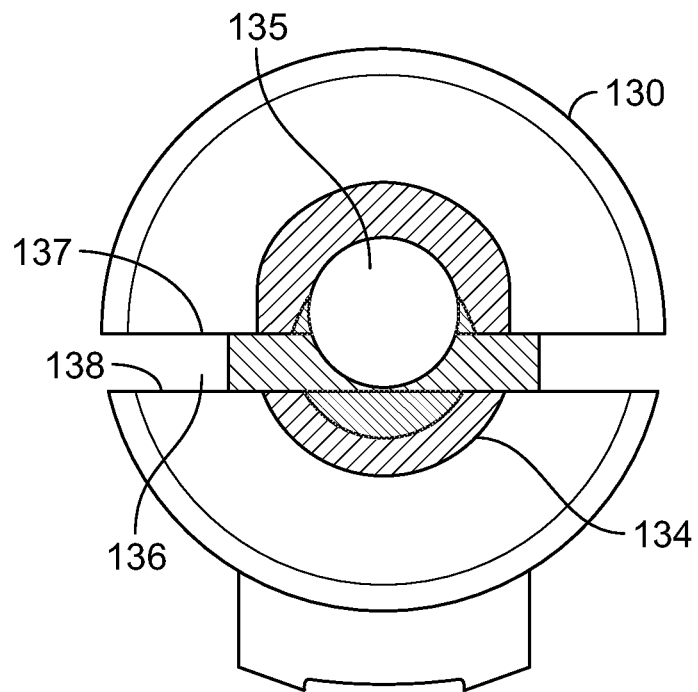
FIG. 4 shows a front view of the guide of FIG. 1.

The post 130 is linear along its length and is centered on an axis that is at an angle relative to an axis running through the length of the shaft 110. The angle as shown in FIG. 2B is approximately 30 degrees. In a variant, the angle can be less than or greater than 30 degrees. Also shown in FIG. 2B, a longitudinal axis of the post is offset from the attachment location between the post 130 and the shaft 110. The post 130 is cannulated 135 along its length. FIGS. 3B and 4 show that the size of the cannulation of the post varies along the length of the post, with the size increasing toward a free end of the post. Of course, variants contemplate other sizes and patterns of the hole size through the cannulated post 130 along its length. The post 130 also includes a slit 136 extending from a location within the length of the post to the free end distal to the shaft 110. The slit 136 runs through the entire cross section of the post 130, as shown in FIG. 4, and is defined by parallel inner surfaces 137, 138 of the post 130. The slit is positioned at approximately the same location on the cross section of the post throughout its length on the post, as shown in FIGS. 3B and 4. Of course, in variants, the slit can be on a slanted trajectory along its length on the post or in any other conceivable geometric configuration that provides a space between the inner surfaces defining the slit.

Figure 5:
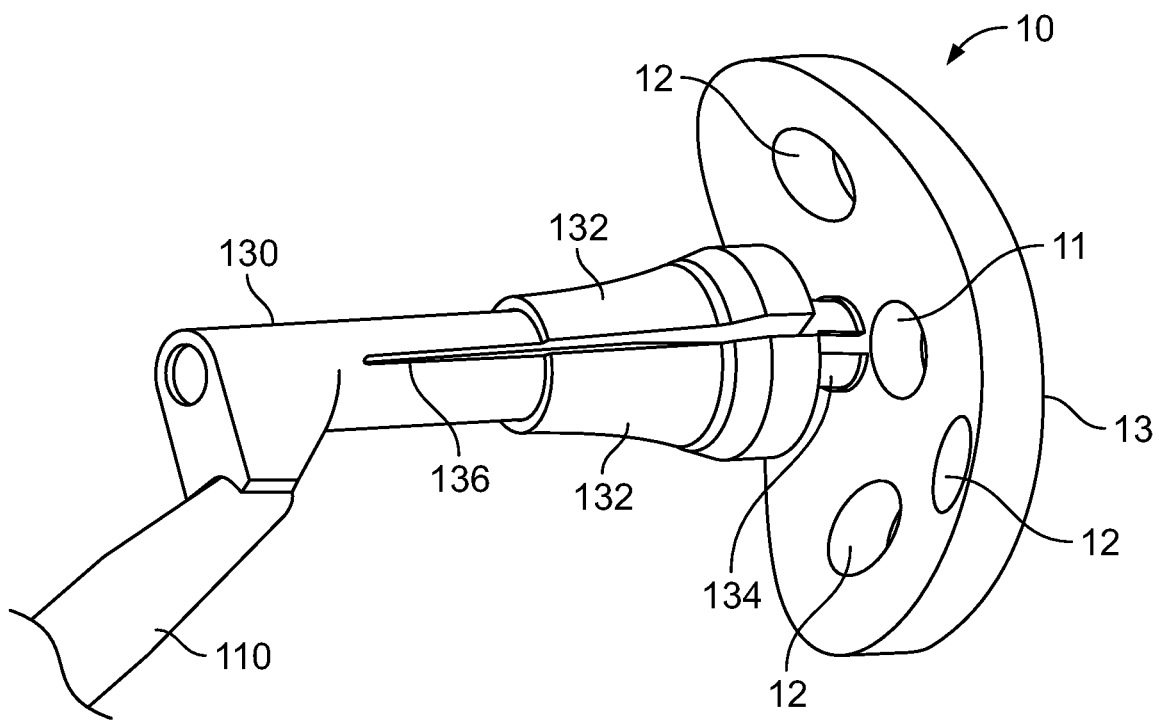
FIG. 5 shows the centering guide shaft of the guide of FIG. 1 adjacent to a surface trial.

The slit divides the post into two leg segments 132. The leg segments 132, as shown in FIGS. 2B, 3B and 4, begin at a first end near the connection between the post and the shaft 110 and extend to a second end at the free end of the post. Each leg segment 132 increases in size over a first distance from the first end to a location between the first and second end, but abruptly decreases in size over a second distance from the location in between the first and second ends and the second end, as best shown in FIGS. 3A and 3B. This smaller portion of the post 130 having a decreased size relative to other parts of the post is an attachment portion 134, as shown in FIGS. 3A, 3B, 4 and 5. Each leg segment 132 is flexible so that when external forces are applied to outer surfaces of the post, particularly outer surfaces along the length of the post corresponding to its longitudinal axis, a space between the leg segments 132 decreases and the legs move closer together. Put another way, a maximum cross sectional dimension of the post 130 at locations corresponding to slit 136 varies as a function of external forces applied to the post 130. The geometry and size of the leg segments 132 is such that the attachment portions 134 are positionable within openings 11 in the surface trial 10, as shown in FIG. 5. When inserted into a hole of the surface trial 10, the post 130 becomes attached to the surface trial. Put another way, the post 130 becomes releasably engaged to the surface trial 10. The increasing sectional size of the post 130 from the first end to the attachment portion 134 also provides support to keep the surface trial engaged when the post is positioned within the surface trial 10 and held against a solid surface, such as that of the glenoid, as is visible in FIG. 5. When inserted into the surface trial 10, the post 130 is partially within a center hole 11, as shown in FIG. 5. The post 130 is adapted for use with surface trials having various sizes and is universal in this regard.

In another embodiment, the post can include two or more slits. Any one of the slits can transect the width of the cross section, either at its widest location or otherwise. The slits can also extend only partially into the cross section from an edge of the post, provided an intersection between slits occurs at an interior location of the post cross section. Put another way, slits intersecting at an internal location on the cross section and extending out to an outer surface of the post are contemplated, which can be considered as multiple slits, or a slit with an irregular outer boundary or edge. In one example, a first slit can transect edge to edge across the cross section of the post, and a second slit can extend from a location on the first slit to a location on the perimeter of the post. Any combination of slits is contemplated and in any geometric alignment, provided there is a continuous gap within each slit to allow flexure and compression of the post. In addition, the length of each slit, where the length is measured in accord with the length of the post, can be linear or it can be irregular. For example, a slit can have an "S" or "Z" appearance along a portion of the length of the post. Of course, any of the variations for slits contemplated in this embodiment can be applied to the single slit described in the above embodiment. In other embodiments, one or more spaces can traverse the cross section of the post having a gap of varying dimension along a length of the one or more spaces. Any complementary inner surfaces of the post that define the space between legs of the post and allow the post to flex and contract when forces are externally applied are contemplated.

In yet another embodiment, the post can include one or more bosses on the attachment portion. The one or more bosses can be sized so that when the post is inserted into the center hole of the surface trial, the boss releasably engages the guide to the surface trial.

In any one of the above embodiments, the post can be of solid construction through its thickness with no cannulation. The post can also be attached to any shaft and/or handle known to those of ordinary skill in the art. In still further embodiments, other structures known to those of skill in the art can be used as a substitute for the cross hair centering guide. In addition, to the extent that the guide can be used without certain elements that are attached directly or indirectly to the post, such constructions are also contemplated herein. For example, the post and shaft alone can be used.

In another embodiment, a guide 200 includes three posts 230, 231A, 231B as best shown in FIGS. 6A through 6C. Two of the posts 231A, 231B are peripheral posts while the third 230 is centrally positioned. Each of the posts is interconnected through a post support 250 of the guide 200. As shown in FIGS. 6A through 6C, a space between peripheral post 231A and the central post 230 is different than a space between peripheral post 231B and the central post 230. Of course, in a variant, the peripheral posts 231A, 231B can both be positioned at a common distance from the central post 230.

Each of the peripheral posts 231A, 231B are sized to fit within holes in the surface trial and include slits that separate each post 231A, 231B into a pair of legs 232A, 232B. At an end of the slits closest the post support 250 the slits terminate in holes 234. The slits in the posts provide flexibility so that the legs flex toward each other when placed into a confined position. Conversely, each leg 232A, 232B returns to an unconfined position when removed from the confined position. Each of the peripheral posts 231A, 231B and the central post 230 is cannulated. The central post 230 includes a boss 233 and an end portion 235 distal to the post support 250 at a free end, as best shown in FIG. 6A. The boss 235 is sized to be releasably engagable inside a corresponding hole 21, 27 in the surface trial 20 through friction. This ensures that the surface trial is secured to the guide 200 during use including when it is placed on a glenoid surface, but at the same time can also be removed with ease when needed. The guide 200 is adapted to attach to various sizes of surface trials, and is therefore universal in this regard. For example, guide 200 can attach to surface trial 20 or 26, as shown in FIG. 6A.

In yet another embodiment, the guide 300 includes four posts 330, 331A, 331B, 331C, as best seen in FIGS. 7A through 7C. Three of the posts 331A, 331B, 331C are peripheral while the fourth 330 is centrally positioned. Each of the posts is interconnected through a post support 350 of the guide 300. As visible in each of FIGS. 7A-7C, a distance between peripheral post 331A and the central post 330 is different than a distance between peripheral post 331B, 331C and the central post. Of course, in a variant, the peripheral posts 331A, 331B, 331C can be placed at equal or varying distances or any combination thereof relative to the central post 330.

Each of the peripheral posts 331A, 331B, 331C are sized to fit within holes in the surface trial and include slits that separate each post 331A, 331B, 331C into a pair of legs 332A, 332B, 332C, as best seen in FIGS. 7B and 7C. At an end of the slits closest to post support 350 the slits terminate in holes 334. The slits in the posts provide flexibility so that the legs flex toward each other when placed into a confined position. Conversely, each leg 332A, 332B, 332C returns to an unconfined position when removed from the confined position. Each of the peripheral posts 331A, 331B, 331C and the central post 330 is cannulated. The central post 330 includes a boss 333 and an end portion beyond the boss 333 at a free end, as best shown in FIG. 7B. The boss 333 is sized to be releasably engagable inside a corresponding hole in the surface trial through friction. This ensures that the surface trial is secured to the guide 300 during use including when it is placed on a glenoid surface, but at the same time can also be removed with ease when needed. The guide 300 is adapted to attach to various sizes of surface trials, and is therefore universal in this regard.

In some variants of the embodiments illustrated in FIGS. 6A through 7C, the peripheral posts can include legs separated by a gap of any shape sufficient to allow flexibility of the legs, particularly when placed into holes in the surface trial. For example, multiple slits can be included on each post. In other examples, the space between legs can be something other than a slit. For example, a space between the legs of the post can vary along the length of the post. It follows that one or more of these spaces between legs can be included on any particular peripheral post.

In other variants of the embodiments illustrated in FIGS. 6A through 7C, the central post 230 can include a boss of any shape known to those of skill in the art. In still further variants, features other than a boss can be used to connect the central post with a surface trial. For example, the central post can include a slit dividing the post into two legs and extending to a free end. Alternatively, multiple slits can be used.

In any one of the above embodiments, the free end of the post 130 or central post 230, 330 can include a lip structure extending outward from the surface of the post at its tip. This lip can be at varying angles relative to a longitudinal surface of the post. For example, the lip can extend at an angle of 70 degrees relative to a longitudinal axis of the post 130. In another example, the lip can extend at an angle of 110 degrees relative to the longitudinal axis of the post 130. The inclusion of a lip allows for additional retention capability for the guide when engaged with a surface trial. This can also be described as active retention. In embodiments where the perimeter of the post or central post is partitioned by slits or other openings, the lip may include several subparts separated by such slits or openings. The shape of the lip can include a constant thickness. The length of the lip measured on the longitudinal surface of the post or central post can be any amount deemed suitable by the user. In some variants, the lip can extend around the entire perimeter of the post surface. In other variants, the lip can extend over a portion of the outer surface of the post. Still further variants contemplate lip geometry that accommodates the needs of particular surgery.

In any one of the above embodiments, the post, central post or peripheral post can have a plurality of sub-posts extending from an end of the post closest to the shaft or from any point on the length of the post, central post or peripheral post. The sub-posts can be of progressively smaller cross sectional area than preceding sub-posts closer to the shaft. Put another way, such posts can have a telescopic structure. These sub-posts can also include hooks or other protrusions adjacent to a distal tip at the free end, which can serve to engage corresponding features within holes of the surface trial. In still further embodiments, the post, central post or peripheral post can include any cross sectional shape or a varying cross sectional shape along its length.

Another embodiment of the guide is illustrated in FIGS. 12A-15B. As shown in FIG. 12A, guide 400 includes shaft 410 and handle 420. At one end of shaft 410 a cross hair centering guide 470 is attached, and at the other, a post 430 is attached. The guide 400 shares certain features in common with guide 100 described above and shown in FIGS. 1-5. To the extent any features of guide 100 are not described for guide 400 herein, it is contemplated that those features are or can be included in guide 400. FIG. 13A shows the post 430 of the guide 400 in greater detail. As with guide 100 described above, post 430 includes two leg segments 432 separated by a slit 436. The slit is defined by mirrored surfaces 437, 438 that are substantially planar with the exception of a central portion representing an end of a cannulation 435 at a free end of the post 430, as shown in FIG. 13B. Each leg segment tapers outward from an end of the post 430 closest to shaft 410 toward a free end and is flexible so that under an external load, the leg segments move toward one another reducing the distance between the mirrored surfaces 437, 438. On an end face of the leg segments 432 facing the free end of the post 430 are attachment portions 434 extending from the end face, as visible in FIGS. 13A and 13B. The attachment portions 434 are nearly as wide as slit 436, but are narrow relative to the leg segments 432 in an axis perpendicular to a plane through the slit 436. At the end of the attachment portions 434 distal to the leg segments 432 are extensions 491, as seen in FIGS. 12B, 13A and 13B. The extensions are narrower than the attachment portions 434 when measured parallel to the plane through the slit 436, as shown in FIG. 13B. The extensions 491 also taper towards a tip so that ends of the extensions are pointed and when viewed from one side include a triangular shape. The taper of each extension is in an opposite direction so that the extensions taper away from one another. At the tip of each extension is a lip 492. The lips 492 extend transverse to a length of the post 430 and away from its longitudinal centerline. As mentioned above, the post is cannulated 435. The cannulation 435 is visible as it appears from the shaft end of the post 430 in FIG. 13C and from the free end of the post in FIG. 13B.

Figure 15A:
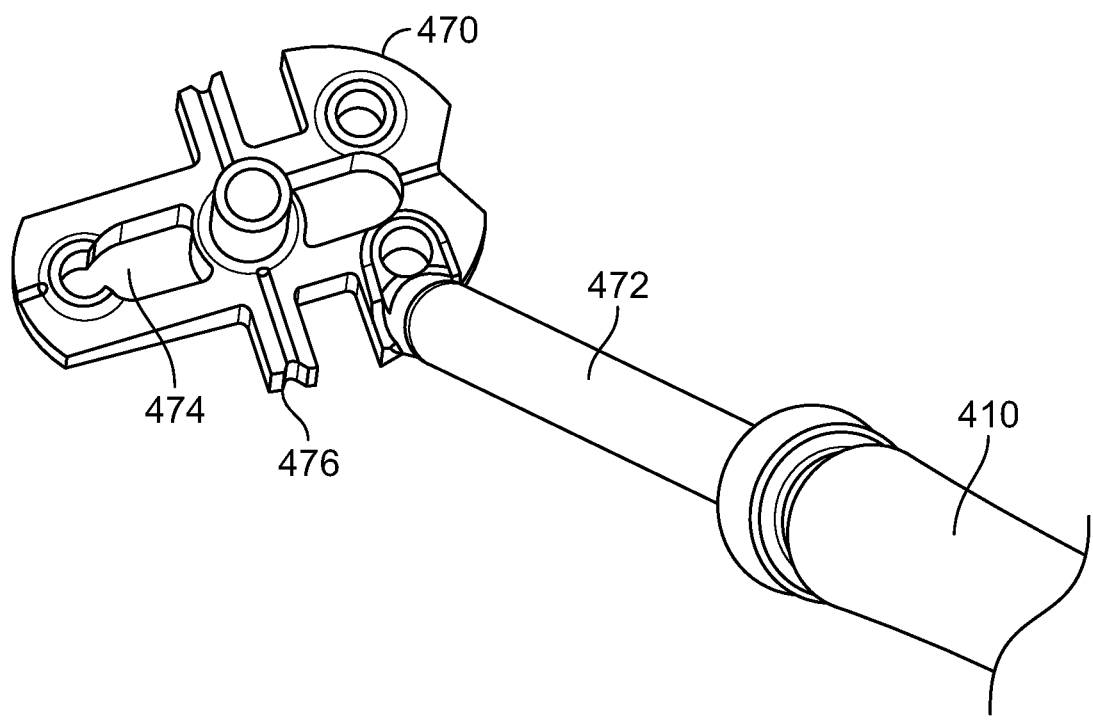
FIG. 15A shows a perspective view of a cross hair centering guide of the guide of FIG. 12A.
Figure 15B:
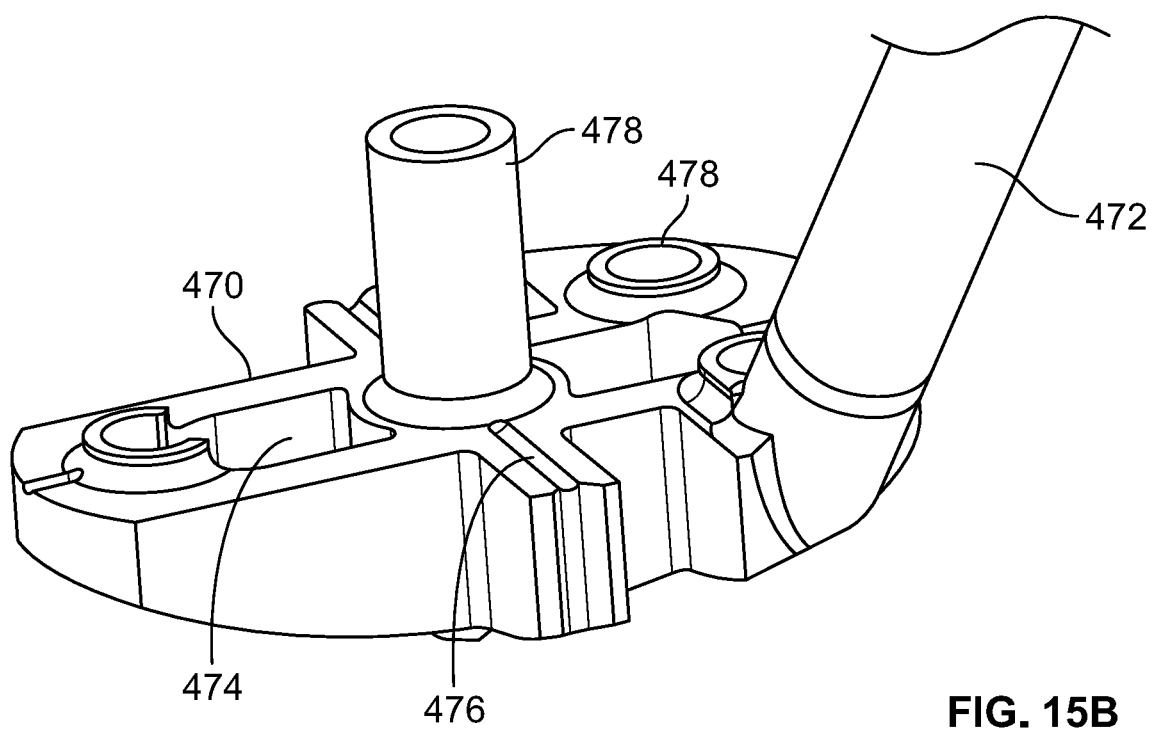
FIG. 15B shows a close up perspective view of the cross hair centering guide shown in FIG. 15A.

At an end of the guide 400 opposite post 430 is the cross hair centering guide 470, as visible in FIG. 12A, and in greater detail in FIGS. 15A and 15B. The cross hair centering guide 470 is connected to shaft 410 of the guide 400 through an extension of the shaft 472. The cross hair centering guide 470 includes a plurality of holes 474 and slots 476. In addition, some of the holes include protrusions 478. All of these features are shown in FIGS. 15A and 15B. The structural features of the cross hair centering guide 470 are arranged so that the guide can be used as a trial or as a cutting guide.

Post 430, as with posts described in the above embodiments, can engage a trial, such as trial 40. Guide 400 is shown with trial 40 attached in FIGS. 12B and 14A. Trial 40 including hole 41 is shown in isolation in FIG. 14B. In one variant, the trial 40 can be translucent. As shown in FIG. 12B, extensions 491 of post 430 extend through the hole 41 of the trial 40 when the trial is engaged to post 430, compressing the leg segments 432 of the post 430 so that each leg segment 432 moves toward the other. When fully inserted through the trial and engaged with it, the end face of the leg portions 432 is either flush or nearly flush with an inward facing surface of the trial 40, as visible in FIG. 14A. In this way, walls defining the hole 41 in the trial 40 surround a majority of a surface area of the attachment portion 434 and the lip 492 of each extension 491 extends toward an outward facing surface of the trial, as seen in FIG. 12B. The lip 492 of each extension 491 provides engagement between the post 430 and the trial 40 over and above the engagement provided by the resistance between the attachment portions 434 and the trial 40 as the attachment portions expand towards walls of hole 41 in the trial 40 in the inserted and engaged position.

In another embodiment, one or more of the post, central post or peripheral post can include a spring loaded device in place of a slit. In this arrangement, the outer surface of the post along its length is solid and not traversed by openings for flexure. However, as with other embodiments, each of the post, central post and peripheral post is cannulated allowing for visualization. The spring loaded device can be positioned within the surface of the attachment portion near the free end of the post and oriented so that its movable component extends outward from the surface of the post. In this way, a maximum cross sectional dimension of the post 130 at the location of the spring can vary as a function of external forces applied to the post at that location. Of course, two or more spring loaded devices can also be included on the post. Spring loaded devices can be placed in any location and in any arrangement on the post, but are typically arranged to be complementary with counterpart surfaces on an inner wall that defines the holes of a surface trial to be used. When inserted into a hole of a surface trial, the spring loaded device operates to engage a recess within the inner wall or walls of the hole. When the spring is released inside the hole, it engages with the recess and as a result, provides securement between the guide and the surface trial. In one example, the spring loaded device is a ball detent mechanism. The ball detent mechanism retracts when first inserted into a hole of a surface trial, and expands when it aligns with a complementary recess or other shape on an inner wall of the hole.

In yet another embodiment, at least one of the post, central post or peripheral post can include surface protrusions in place of a slit or slits. The surface protrusions can extend across any part or portion of a longitudinal surface of the post. Where the post includes such protrusions, complementary features are included on the inner walls of the hole or holes of the surface trial to facilitate engagement when the guide is inserted into the surface trial. In one example, the protrusions extend over a length from a first location adjacent to the free end to a second location on the length of the post, the distance between being approximately equal to the thickness of surface trial or trials anticipated to be used in conjunction with the guide. Examples of protrusion types that can be incorporated into the surface of the post include teeth, grooves, screw threads, flanks, splines or knurling. In a variant of any one of the above embodiments, the structural features of any one of the post, central post or peripheral post can be complemented by the use of materials that provide the post with additional elasticity. When a post made from relatively elastic materials is inserted into a hole of a surface trial, engagement can be improved between the post and a surface trial due to the expansion of the post within the hole and the resistance to expansion caused by friction with the walls of the hole. Other ways of using materials are also contemplated. For example, any one of the post, central post or peripheral post of the guide can have material properties that promote engagement between a surface of the post and the surface trial when the post is positioned within a hole of the surface trial.

The embodiments above describe guides with one, three or four posts. Of course, guides with two posts or five or more posts are also contemplated. In other embodiments, each of the central post and peripheral posts in multiple post guides can include any one of the engagement features described above. Also, any one of the central post or the peripheral posts can be of a solid structure or be cannulated. Put another way, within each guide, each post can include features for releasable engagement or attachment to a surface trial that are unique relative to other posts on the same guide.

In any of the above embodiments, the overall shape and/or geometry of the post, including the cross sectional shape, the shape of the length, the orientation relative to the shaft, slits, bosses, spring mechanisms and any other general feature, can be modified as desired to suit surgical preferences or to meet other needs. Similarly, the structure of the handle, shaft, and cross hair centering guide can also be modified as seen fit. It is also contemplated that features of particular embodiments can be used in combination with features from other embodiments.

Advantages of the described system include that the guide functions as a universal attachment to a surface trial. Because only a single guide is needed to assess implant and fastener hole locations for various surface trials, the system makes it substantially easier to evaluate different options for an implant. The system also provides a visual indication of the bone surface that allows for the determination of a true center of the bone surface at the joint. Visualization of the bone surface is possible through the translucent surface trial and also through the cannulated posts of the guide. Through the cannulated posts, a surgeon can identify a center for a pilot wire or fastener locations for the placement of holes. In addition, the placement of a pilot wire through the center replaces the need to drill a centering hole in the bone and thus minimizes the difficulty of bone surface preparation. Another advantage of placing a pilot wire is that no marking implement or marking action is required to identify the center of the bone surface because a pilot wire can be placed during initial identification of the center of the bone.

Other advantages of the system include the small size of the guide which allows for better visualization of the surface trial and therefore an improved ability to understand and establish a desired implant size and placement location for an implant. The system also serves to provide a much improved means of identifying a placement location for an implant because when placed on the bone, the surface trial is fully seated on the bone surface. The selected surface trial will be the same size and shape as the implant, thus providing a visual understanding to the user of how the implant will nest on the bone surface. As an added advantage, fewer tools are required to complete the described system than with conventional systems.

Figure 8:
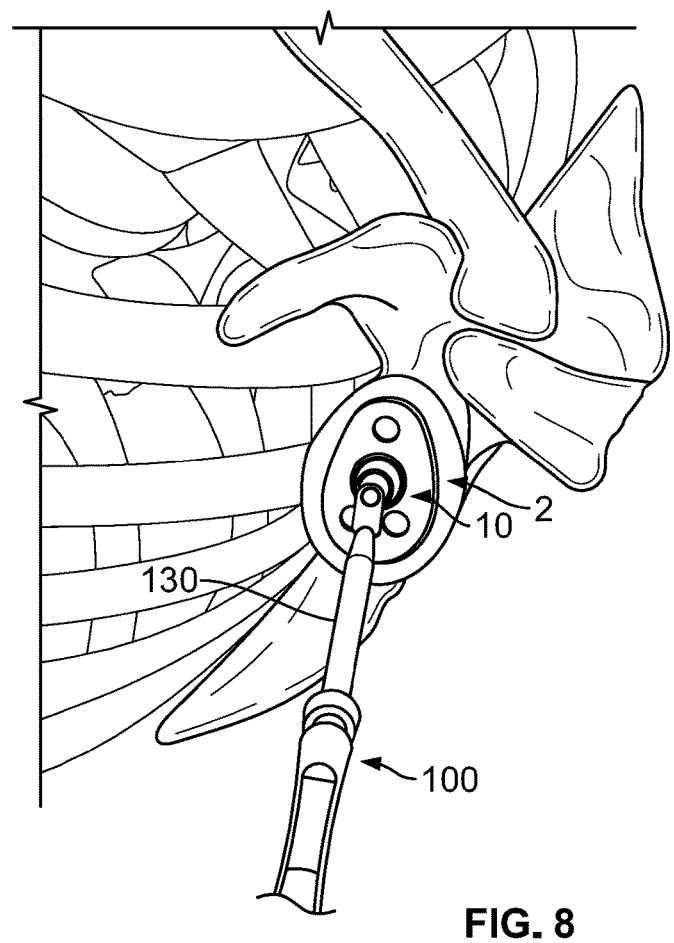
FIG. 8 shows a method embodiment step where the centering guide system is positioned onto the glenoid surface.

In another aspect, the centering guide system is used in a method of positioning a pilot wire for joint repair. Exemplary applications of the system include total shoulder arthroplasty and procedures for the hip, knee, ankle and spine joints. The system also functions to assess congruency of the surface trial after reaming or resecting of the bone surface. As a corollary, the surface trial on the reamed or resected bone surface can also be assessed to confirm the accuracy of implant fastener locations based on the position of the holes of the surface trial on the bone. The overall process of using a surface trial, reaming and placing an implant is described in U.S. Pat. Pub. No. 2015/0265292, hereby incorporated by reference herein in its entirety. In a first embodiment, and as best seen in FIGS. 5 and 8, the guide 100 is attached to the translucent surface trial 10 by inserting the attachment portion 134 of the post 130 into the center hole 11 of the surface trial 10. As described above, the post 130 includes a slit to provide flexibility and to allow insertion of the guide into the surface trial. In a variant, the post can include other features to provide stable attachment to the center hole 11 of the surface trial 10. Once attached, the guide 100 is releasably secured to the surface trial 10. In this position, an outside surface 13 of the surface trial opposite the guide remains uninterrupted by the guide as the attachment portion 134 of the post does not extend beyond the center hole 11 of the surface trial in its secured position. The centering guide system of this embodiment is used for shoulder arthroplasty surgery, however, other applications are contemplated, including at least those described in other parts of the specification.

Figure 9:
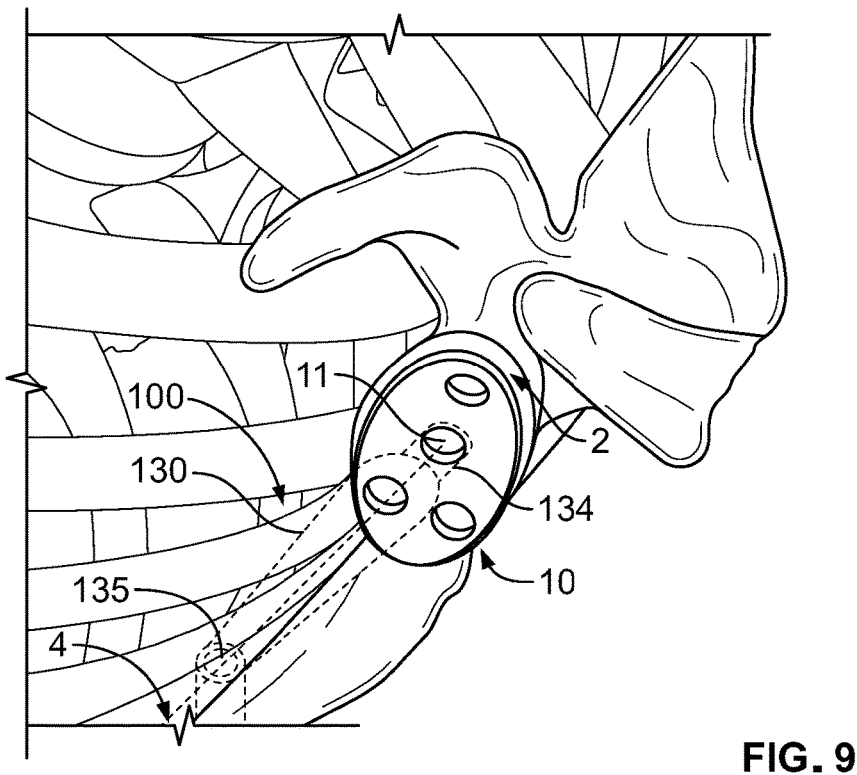
FIG. 9 shows another step in the method of FIG. 8 where the surface trial is visible as positioned on the glenoid by illustrating the guide in phantom.

With a surgical site at the glenoid of a patient prepared, the centering guide system, including the guide 100 and attached surface trial 10, is placed over a glenoid surface 2. This step is shown in FIG. 8 and involves manipulation of the guide 100 to position the surface trial 10 directly on the glenoid surface 2. Because the post 130 of the guide 100 does not protrude from the outside surface 13 of the surface trial 10 in its attached position, the surface trial 10 sits flush with the surface of the glenoid 2 once the surface trial is in position and in contact with the glenoid 2. FIG. 9 illustrates how this appears with the location of the guide 100 holding the surface trial 10 shown in phantom.

To refine the position of the surface trial 10 on the glenoid surface, a user views the glenoid surface through the cannulation 135 of the post 130. The position for viewing the glenoid through the cannulation 135 is shown in FIG. 9. When a visual inspection through the cannulated post and through the translucent surface trial 10 establishes that the surface trial should be repositioned, the guide 100 is manipulated to adjust the position of the surface trial 10 as necessary to establish a desired centering location. One exemplary way the guide 100 can be adjusted is by manipulating the handle 120. Because the surface trial 10 in place over the glenoid emulates the size and shape of an implant, the user can visualize the final implant fastener locations and a center location for a pilot wire based on the position of the surface trial. For example, peripheral holes 12 allow visualization of fastener locations on the glenoid surface. In addition, because the surface trial nests within the glenoid surface, the user gains knowledge of how the implant will be seated and otherwise fit on the surface of the glenoid based on the contours it exhibits at the time of assessment. Again, FIG. 9 shows how the user can view various locations on the glenoid through the system including surface trial. Establishment of the final implant location involves many considerations, including identification of locations for fasteners based on fastener alignments that coincide with a relatively larger amount of bone in the scapula. Thus, the features of the system as described herein are significant in their capacity to minimize error in the identification of entry points for the fixation of an implant.

At this juncture, if the user adjusting the position of the surface trial 10 on the glenoid 2 using the guide 100 determines that the current surface trial 10 is inappropriate for the patient for any reason, such as the trial having a non-compatible size and shape, the guide 100 is removed from the surgical site and the surface trial 10 is replaced with another deemed to be more suitable, such as one having larger or smaller dimensions. To accomplish this step, because the guide is universal, the user can simply detach the current surface trial and then attach another to the same guide using the steps as described above. Insertion of the attachment portion 134 of post 130 into a surface trial 10 is shown, for example, in FIG. 5.

Figure 10:
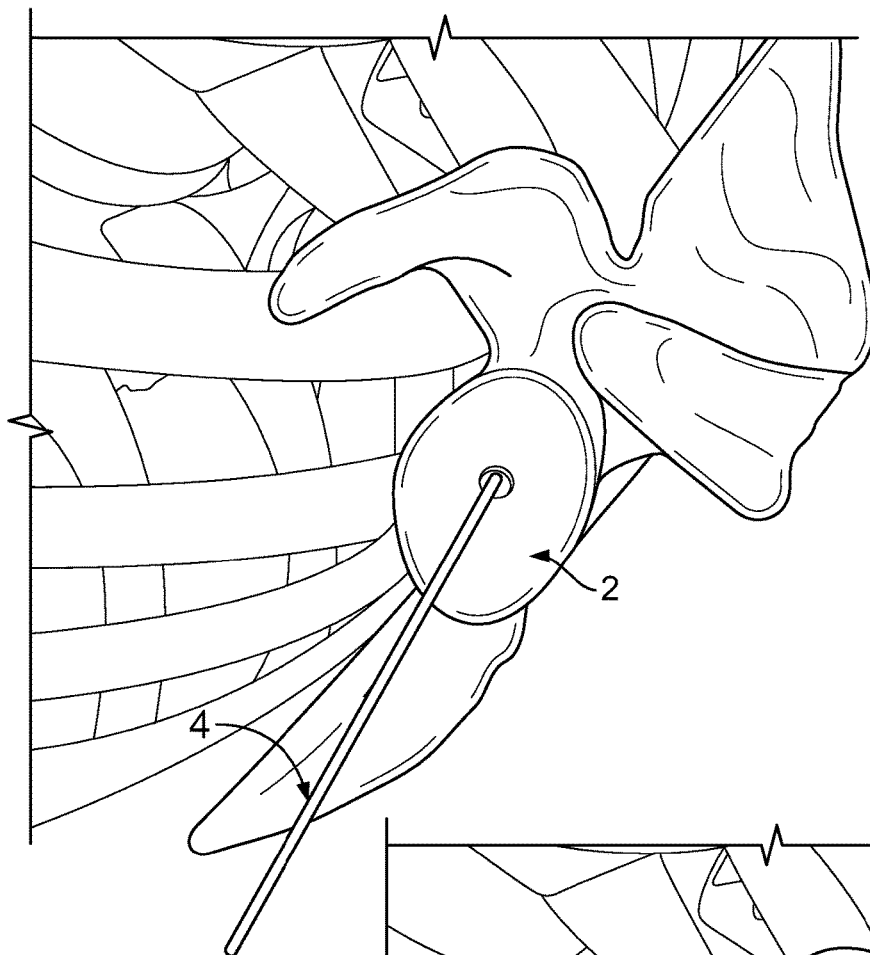
FIG. 10 shows another step in the method of FIG. 8 where the glenoid surface is visible as it appears after placement of a pilot wire with the centering guide system removed.

If the surface trial 10 attached to the guide 100 and in place on the glenoid 2 is deemed suitable for the patient, then the cannulation 135 through the post 130 is used to finalize and confirm a centering location on the glenoid 2. Once confirmed, a pilot wire 4 is placed through the cannulation 135 of the post 130, through the centering hole 11 of the surface trial 10, and then through the glenoid 2 bone itself. The trajectory of the pilot wire 4 into the glenoid 2 is shown in FIG. 9 and the pilot wire as implanted in the glenoid is shown in FIG. 10. The method of implantation of the pilot wire into the glenoid bone is by any means known to those of skill in the art. Either prior to or following pilot wire placement, peripheral fastener locations are marked through holes 12 for later alignment of the implant.

Figure 11:
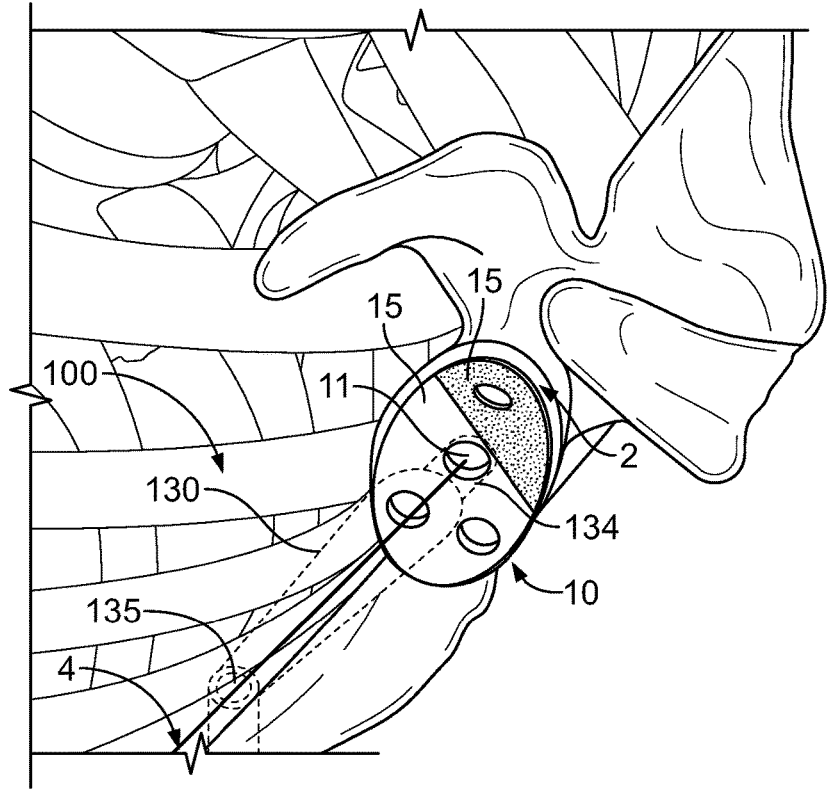
FIG. 11 shows another step in the method of FIG. 8 where the surface trial is placed onto the glenoid after reaming. A variation in the appearance of the translucent surface trial material is visible to indicate inconsistencies in the congruency between the surface trial and the glenoid surface.
Figure 14A:
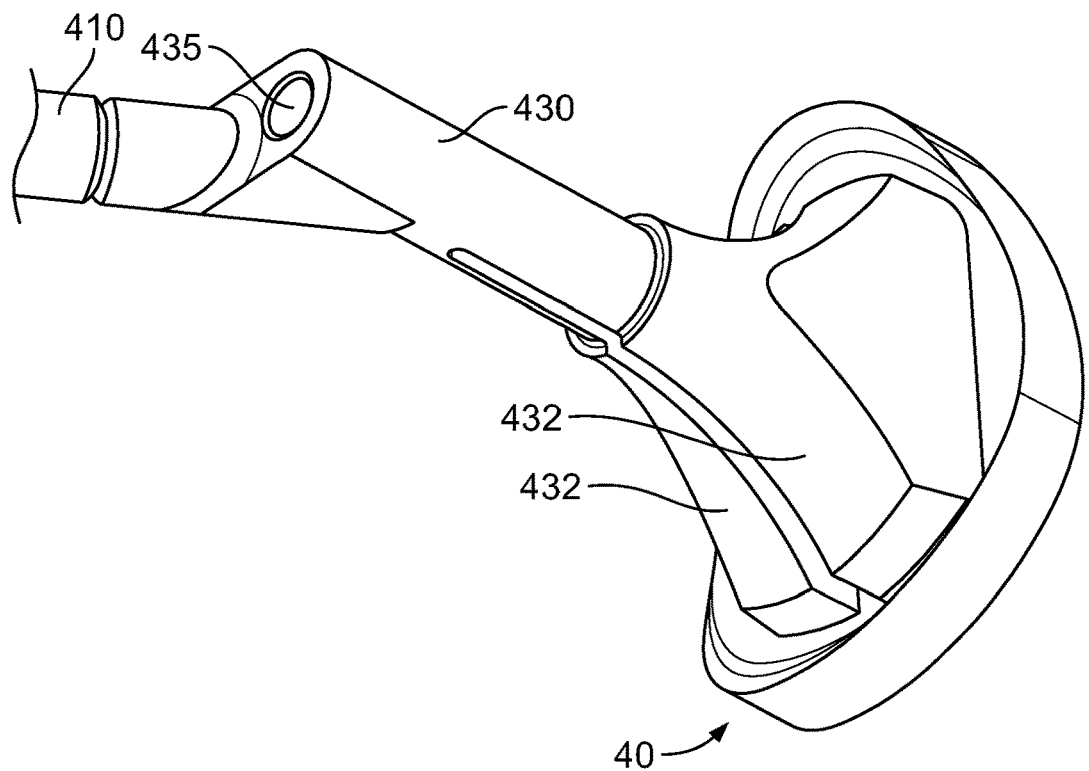
FIG. 14A shows a side perspective view of the post of the guide of FIG. 12A with the trial attached.
Figure 14B:
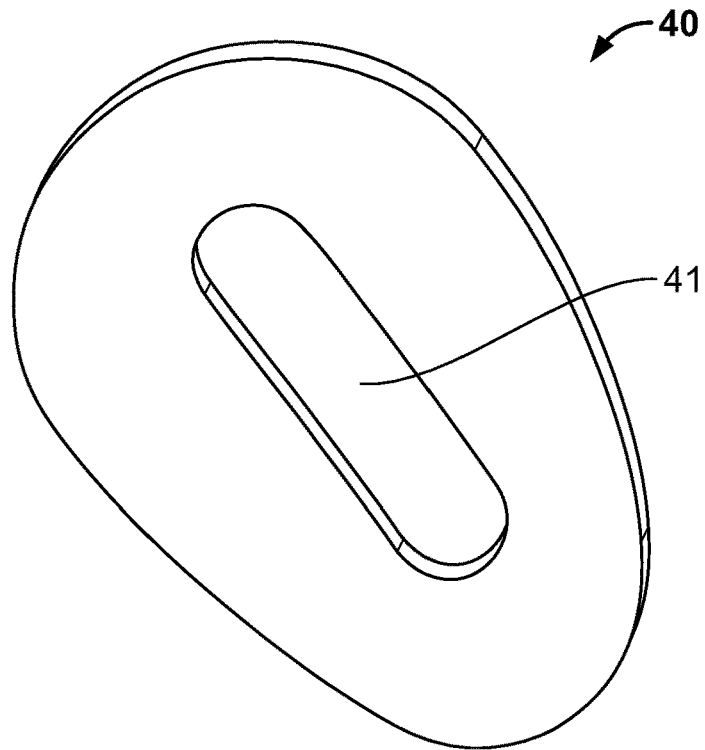
FIG. 14B shows a perspective view of the trial shown in FIG. 14A.

When the pilot wire 4 is secured in place in the glenoid 2, the glenoid guide system is removed from the surgical site so that only the pilot wire 4 remains. A reaming operation is then performed (not shown) over the pilot wire 4 into the glenoid bone 2. The reaming procedure revises the glenoid surface as needed to increase the surface area of the glenoid in contact with the implant and overall to provide a surface better suited to seat the implant. Of course, reaming is performed until subchondral bone is exposed. Upon completion of reaming, the guide 100 with attached surface trial 10 is once again placed onto the glenoid 2 as before and the guide 100 is used to adjust the position of the surface trial 10 to center the surface trial on the glenoid 2. Congruency of the glenoid 2 surface is assessed by viewing any variability in the appearance 15 of the translucent surface trial 10 when it is in position on the glenoid 2, as shown in FIG. 11. Blood spots on the surface trial can also be used to evaluate congruency of the surface. The surface trial can also be used to verify conformance of the holes 12 with the implant fastener locations established based on the markings previously made on the bone surface. In a variant, the step of assessing congruency can alternatively or additionally be performed before the pilot wire is placed into the glenoid.

Following confirmation that the glenoid surface 2 is shaped to match the implant and therefore in the proper position, the implant corresponding to the translucent surface trial 10 used is procured and prepared for implantation at the surgical site. Securement of an implant on a resected bone surface is described in detail in U.S. Pat. Pub. No. 2015/0265292. Of course, to the extent there is any lack of congruency between the surface trial and the glenoid surface, additional reaming is performed as necessary followed by additional assessment of surface congruency using the surface trial as described in the steps above.

In another embodiment, the method of positioning a pilot wire and marking a bone for an implant can be performed using the guide 400. The method is as described above, but also includes additional means of engagement between the post 430 and the trial 40 through the lips 492 located on the tips of the extensions 491 when the attachment portions 434 are through a hole 41 in the trial 40.

In another embodiment, the method of positioning a pilot wire can be performed using a guide having a center post and one or more peripheral posts. For example, the guide can be as shown in FIGS. 6A through 6C or as shown in FIGS. 7A through 7C. The steps of the method using these guides 200, 300 can be the same as described above, although the peripheral posts, to the extent one or more peripheral fastener locations are sought to be identified, can be used for the identification of fastener locations on the glenoid. For example, when the centering guide system is placed onto the glenoid 2, cannulations in the posts 231A, 231B can be used to visualize fastener locations for superior and inferior locations 22, 28 on the glenoid in addition to cannulated post 230 used for determining the center location 21, 27. Visualization of the glenoid surface through the peripheral posts can be performed before or after visualization of the glenoid surface at the central post. In one example, identified fastener locations are marked for later verification of implant alignment. In other examples, the cannulated posts 230, 231A, 231B can also be used to visualize the glenoid surface after the reaming process is completed and the centering guide system is placed back onto the glenoid.

In yet another embodiment, the centering guide system of any one of the above embodiments can be used with a trial that is not translucent or without any surface trial. In other embodiments, it is contemplated that the systems described herein can be utilized for pilot wire placement and implant preparation on any concave shaped articular bone surface having a physical size compatible with the system described herein.

Advantages of the method of using the centering guide system include that the translucent surface trial provides visibility that allows for accurate identification of a center for the placement of the pilot wire. After the trial is initially removed and the bone is reamed over the pilot wire, the translucent aspect of the surface trial can once again be used to determine the congruency of the bone surface by assessing variations in the shade or color of the surface trial when it is seated on the bone surface, enhancing the congruency for the implant itself. Yet another advantage of the methods described herein is that the translucent surface trial sits flush with the bone surface when placed in position on the bone and the edges of the surface trial are visible to the user with no obstructions. This allows for a better assessment of the bone surface for pilot wire placement and implant fastener visualization and for overall placement of an implant. These advantages derive from the way the posts grip the surface trial from inside surfaces of the hole or holes on the trial in stark contrast to conventional guides that grip onto the outer articulating surface or outer perimeter of surface trials.

The invention described herein provides at least four advantages. First, one guide can be used that matches all implant sizes. See FIG. 5, for example, illustrating how the attachment portion 134 of the post 130 can be used for a variety of surface trials. Second, the system allows for visualization of all implant fastener locations. See, for example, FIGS. 5-8. Third, a user can visualize the edges of any implant. See, for example, FIGS. 8-11. Fourth, the contours of the bone surface can be assessed in detail. See, for example, FIG. 11.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A guide system for resecting a bone surface in a desired location comprising:
   a surface trial having at least one hole, the surface trial positionable on the bone surface;
   a centering guide post having a first location on its length with an outer cross sectional dimension that varies between a maximum and a minimum as a function of a force applied to an outer surface of the centering guide post from outside of the centering guide post, the centering guide post including a slit that separates the centering guide post into first and second segments that are insertable into the at least one hole of the surface trial so that the centering guide post is releasably engageable to the surface trial, wherein the outer cross sectional dimension at the first location varies according to a position of the centering guide post within the at least one hole of the surface trial, wherein the outer cross sectional dimension at the first location decreases with an increase in the force applied to the outer surface of the centering guide post, wherein the slit has a width dimension extending between the first segment and the second segment measured absent the force applied to the outer surface, the width dimension varying between a first end of the slit remote from free ends of the first and second segments and a second end of the slit at the free end of at least one of the first and second segments, the width dimension being a first width at a second location between the first end of the slit and the second end of the slit and a second width at the second end of the slit, the first width being less than the second width, wherein the slit has a first lateral dimension from the second end of the slit to a third location between the second end of the slit and the second location and a second lateral dimension at a fourth location between the third location and the first end of the slit, the second lateral dimension being greater than the first lateral dimension, the first and second lateral dimensions being measured in a direction orthogonal to both the width dimension and the length of the centering guide post; and a centering guide handle attachable to the centering guide post, wherein when the centering guide post is releasably engaged to the surface trial, the centering guide handle is adapted to position the surface trial on the bone surface and the centering guide post is adapted to allow visualization of a position of the surface trial on the bone surface.

2. The guide system of claim 1, wherein a distance from the first end of the slit to the second end of the slit is less than the length of the centering guide post, and wherein the first and second leg segments are flexible to adjust the outer cross sectional dimension of the centering guide post such that a separation distance between the first and second leg segments decreases when the centering guide post is placed into the at least one hole of the surface trial.

3. The guide system of claim 1, wherein the surface trial is translucent.

4. The guide system of claim 2, further comprising a lip attached to at least one of the first and second segments of the centering guide post, the lip extending from at least a portion of the outer surfaces of the centering guide post.

5. The guide system of claim 1, further comprising a centering guide structure attached to the centering guide handle so that the centering guide structure is positioned at a first end of the centering guide handle and the centering guide post is positioned at a second end of the centering guide handle opposite the first end, wherein the centering guide structure is adapted to nest on the bone surface.

6. The guide system of claim 2 wherein the slit is defined by inner surfaces of the first and second leg segments and further wherein one of the inner surfaces is located at approximately the same location on the cross section of the centering guide post at any point from the first end to the second end of the slit.

7. The guide system of claim 3, wherein the centering guide post further comprises at least one ball detent mechanism adapted for engagement with a recessed surface within a hole of the at least one hole of the surface trial.

8. A guide for use in preparation for resection of a bone surface in a desired location comprising:

a cannulated centering guide post cannulated throughout its length, wherein at least a portion of the cannulated centering guide post is flexible so that an outer cross sectional area of the cannulated centering guide post at one or more locations on the portion of the cannulated centering guide post decreases when subject to a forces applied to an outer surface on the portion of the cannulated centering guide post from outside of the cannulated centering guide post, the cannulated centering guide post comprising:

a slit separating the cannulated centering guide post into first and second leg segments, the slit extending from a first end of the centering guide post to a second location, a distance from the first end to the second location being less than the length of the cannulated centering guide post, the slit being coextensive with part of the cannulation of the cannulated centering guide post, wherein the first leg segment includes a first surface facing the second leg segment, the first surface including a central part in between two lateral parts, the central part being recessed relative to the two lateral parts such that an obstruction of the cannulation due to the first leg segment is minimized when the force applied to the outer surface of the portion of the cannulated centering guide post brings the first and second leg segments closer to each other, and wherein when the first and second leg segments are measured in section, the first leg segment has a first shape and the second leg segment has a second shape different from the first shape.

9. The guide of claim 8, wherein the cannulated centering guide post includes an inner diameter defining the cannulation, the inner diameter varying along the length of the cannulated centering guide post.

10. The guide of claim 8, wherein the cannulated centering guide post includes a first end adapted to actively retain a surface trial when the cannulated centering guide post is inserted into the surface trial.

11. The guide of claim 10, further comprising a lip attached to the first end of the cannulated centering guide post and extending outward from the outer surface of the cannulated centering guide post, the lip at an angle relative to the outer surface such that the lip retains a surface trial when the cannulated centering guide post is inserted through one hole of an at least one hole of the surface trial.

12. The guide of claim 8, further comprising a ball detent mechanism on the portion of the cannulated centering guide post, the ball detent mechanism adapted to fit into a complementary shape within one hole of an at least one hole of a surface trial when the cannulated centering guide post is placed into the surface trial.

13. A method of using a guide system for resecting a bone surface in a desired location, the method comprising:

using a centering guide handle to insert a first end of a centering guide post into a hole in a surface trial, the centering guide post attached to the handle, wherein the centering guide post is cannulated throughout its length and adapted to engage the surface trial when inside the hole, a cross sectional dimension of the centering guide post at the first end decreasing upon application of external forces onto an outer surface of the centering guide post from outside of the centering guide post during insertion of the first end into the hole;

contacting the bone surface with a contact surface of the surface trial; and placing a pilot wire through each of the cannulation of the centering guide post, the hole of the surface trial and the bone.

14. The method of claim 13, wherein engaging the surface trial when the centering guide post is inside the hole of the surface trial further comprises frictional engagement between the centering guide post and the hole of the surface trial as the centering guide post is restrained from expanding due to an inner wall defining the hole of the surface trial.

15. The method of claim 13, wherein engaging the surface trial when the centering guide post is inside the hole involves securement of the surface trial by a lip attached to the first end of the centering guide post, the lip extending from a body of the centering guide post in a direction distal to the centering guide post surface.

16. The method of claim 13, further comprising the steps of:

removing the surface trial using the centering guide handle;

inserting a reamer over the pilot wire and into the bone;

removing the reamer; and replacing the system onto the bone using the centering guide handle.

17. The method of claim 16, wherein inserting the first end of the centering guide post into the hole in the surface trial causes two leg segments of the centering guide post to flex so that a distance between each leg segment decreases.

18. The method of claim 16, wherein inserting the first end of the centering guide post into the hole in the surface trial causes a boss attached to the centering guide post to become releasably engaged to an inner wall defining the hole of surface trial.

19. The method of claim 16, further comprising the step of viewing the surface of the bone through the surface trial after replacing the surface trial on the bone, the surface trial being translucent.

\* \* \* \* \*